United States Patent [19]

Forster et al.

[11] Patent Number: 5,753,797
[45] Date of Patent: May 19, 1998

[54] PHOTO-ACOUSTIC GAS SENSOR AND ITS MANUFACTURE AND USE

[75] Inventors: Martin Forster, Jona; Rolf Pleisch, Hegnau-Volketswil; Mourad Baraket, Stäfa, all of Switzerland

[73] Assignee: Cerberus AG, Switzerland

[21] Appl. No.: 706,240

[22] Filed: Sep. 4, 1996

[30] Foreign Application Priority Data

Apr. 9, 1995 [EP] European Pat. Off. ............ 95113854

[51] Int. Cl.$^6$ ................................................ G01N 29/02
[52] U.S. Cl. .................... 73/24.01; 250/343; 73/24.02
[58] Field of Search .......................... 73/24.01, 24.02; 250/343

[56] References Cited

U.S. PATENT DOCUMENTS

| Re. 34,828 | 1/1995 | Sirker | 210/137 |
|---|---|---|---|
| 3,602,759 | 8/1971 | Evans | 313/112 |
| 3,820,901 | 6/1974 | Kreuzer | 356/425 |
| 3,938,365 | 2/1976 | Dewey, Jr. | 73/24.02 |
| 4,051,372 | 9/1977 | Aine | 73/24.02 X |
| 4,200,399 | 4/1980 | Kimble et al. | 73/24.02 X |
| 4,557,137 | 12/1985 | Kitamori et al. | 73/61.79 |
| 4,557,603 | 12/1985 | Oehler et al. | 356/418 |
| 4,657,397 | 4/1987 | Oehler et al. | 356/414 |
| 4,740,086 | 4/1988 | Oehler et al. | 356/432 |
| 4,818,882 | 4/1989 | Nexo et al. | 250/343 |
| 5,125,749 | 6/1992 | Leugers et al. | 356/432 |
| 5,129,255 | 7/1992 | Corbin | 73/24.02 |
| 5,141,331 | 8/1992 | Oehler et al. | 73/24.01 X |
| 5,285,677 | 2/1994 | Oehler | 73/24.01 |
| 5,339,674 | 8/1994 | Hammerich et al. | 73/24.02 |
| 5,454,968 | 10/1995 | Nalette et al. | 252/192 |
| 5,616,826 | 4/1997 | Pellaux et al. | 73/24.02 |

FOREIGN PATENT DOCUMENTS

| 0151474 | 7/1991 | European Pat. Off. |
| 3509532 | 9/1986 | Germany. |
| 3817791 | 12/1989 | Germany. |
| 679076 | 12/1991 | Switzerland. |
| 2190998 | 12/1987 | United Kingdom. |

Primary Examiner—Hezron E. Williams
Assistant Examiner—Jay L. Politzer
Attorney, Agent, or Firm—Brumbaugh, Graves, Donohue & Raymond

[57] ABSTRACT

A photo-acoustic gas sensor for measuring a gas concentration, e.g., of an explosive gas, consists of a cylindrical sensor body (1) which includes a cylindrical measurement chamber (13) whose longitudinal axis extends perpendicular to the longitudinal axis of the cylindrical sensor body. Without changing the outer dimensions of the sensor body, the length of the measurement chamber can be changed in accordance with a desired measurement sensitivity and a desired measurement range. A light source (5) is disposed such that it irradiates the measurement chamber without irradiating a gas-permeable membrane (2), so that the membrane will not produce an interference signal. The gas sensor is rendered explosion-proof as the light source and a photo-diode (6) which monitors the light source are tightly sealed from the environment. Proper functioning of a microphone (4), the light source and the photo-diode are monitored by analyzing a background signal.

12 Claims, 2 Drawing Sheets

PHOTO-ACOUSTIC GAS SENSOR AND ITS MANUFACTURE AND USE

BACKGROUND OF THE INVENTION

The invention relates to a photo-acoustic gas sensor.

Photo-acoustic gas sensors are used in many areas of research and industry for detecting the presence and concentration of a gas in the ambient, e.g., $CO_2$ methane and other hydrocarbons, and toxic gases. Fields of application include, e.g., process monitoring in laboratories, bioreactors or breweries, monitoring of industrial work areas with respect to maximum work-area concentrations, and measurement of $CO_2$ in fire extinction. Functioning of these gas sensors is based on the photo-acoustic effect, namely the generation of an acoustic pressure wave as a result of irradiation with suitably modulated light, with the magnitude of the wave being directly related to gas concentration. The acoustic pressure wave arises as the gas absorbs the optical radiation and is heated thereby. Periodic thermal expansion and pressure fluctuations result, corresponding to the modulation of the optical radiation. Measurement of the acoustic pressure then permits inferring the gas concentration. Different gases are characterized by the use of light waves of different wavelengths corresponding to the absorption lines of the gases. Used for this purpose are laser sources or wide-band light sources, e.g., spiral-wound glow filaments combined with optical band-pass filters.

Use of the photo-acoustic effect for gas detection affords concentration measurements of particularly high sensitivity. However, a high degree of measurement sensitivity requires guarding against interference signals. Such gas sensors have to be designed with special care, and high production costs may result.

Photo-acoustic gas sensors in current use are disclosed in European Patent Document 0151474 and British Patent Document 2190998, for example. They include a measurement chamber which typically is cylindrical, a wide-band light source, an optical filter, a microphone, and a driver and signal-analyzer electronics unit. Gas enters the measurement chamber either through a gas-permeable membrane or via a supply pipe. The intensity-modulated light emitted by the light source first passes through the optical bandpass filter whose spectral band corresponds to the absorption band of the gas to be detected, and then illuminates the volume of the measurement chamber. If the gas in question is present in the measurement chamber in a sufficient concentration, an acoustic pressure wave is produced in accordance with the photo-acoustic effect, which pressure wave is received by the microphone and converted into an electrical voltage signal. This signal is electronically analyzed for indication of gas concentration.

In such a sensor system, pressure waves may arise which are not produced by the gas, giving rise to an interference signal which is difficult to distinguish from the desired measurement signal. One source of interference is the gas-permeable membrane. The membrane is disposed relative to the light source such that light rays may reach the membrane directly, or also indirectly after reflection from the measurement chamber walls. With the membrane heated along with the gas, the membrane can be set in oscillation and give rise to an acoustic wave. This wave, as well as pressure waves which originate from vibrations of other parts of the sensor and whose frequency is in a range similar to that of the light source modulation, can give rise to interference and noise in the measurement signal. By suitably shaping and directing the beam, the light intensity on the membrane and the resulting interference signal can be reduced. E.g., a divergent beam can be used. But typically, there is residual radiation still reaching the membrane, giving rise to an interference signal especially in the case of high-sensitivity measurements.

While divergence of the light beam and reduction of the light intensity diminish the interference signal caused by the membrane, they also impede optimization of the magnitude of the measurement signal. The magnitude of the acoustic pressure generated depends on the light intensity in the measurement chamber and can be optimized by concentrating the light beam in the measurement chamber. Typically, this is achieved in that a reflector, e.g., an ellipsoidal reflector, is disposed at the light source such that most of the light is focused onto the measurement chamber. If the membrane, too, disposed opposite the light source, light rays reach the membrane directly and without attenuation. Thus, in present-day arrangements, reduction of the interference signal caused by the membrane is difficult to combine with optimization of measurement signal magnitude.

It is known, e.g. from Swiss Patent Document 679076, that the magnitude of the acoustic pressure produced by the photo-acoustic effect is proportional to the absorption density of the optical radiation and inversely proportional to the volume of the measurement chamber. When there is a change in the volume of the measurement chamber, the resulting pressure signal also changes. If the volume is reduced, with gas concentration remaining constant, a larger pressure signal is generated and greater resolution can be achieved in concentration measurement. Thus, the measurement range and measurement sensitivity are influenced by the volume of the measurement chamber. In known designs of photo-acoustic gas sensors, the volume of the measurement chamber is governed in part by the arrangement of the sensor components. I.e., because of the cylindrical shape of the measurement chamber and the arrangement of the membrane, light source and microphone, the system size of the sensor and the outer dimensions of the sensor body are determined by the length and volume of the measurement chamber. If the manufacturer or user wishes to change the volume of the measurement chamber in order to carry out a measurement over a different measurement range and with a different measurement sensitivity, in most cases this would be feasible only by a suitable change of the system size of the sensor and of the outer dimensions of the sensor body. Thus, gas detection by means of a sensor as described, with predetermined size of the measurement chamber, is limited to one measurement range and one measurement sensitivity. Applicability is restricted and can be extended only at additional expense and additional production costs.

Typically, the known gas sensors are costly to manufacture, due in part to their specific areas of application and in part to the need for expensive components, e.g., an optical band-pass filter, and because of the required manual assembly.

SUMMARY OF THE INVENTION

Among objects of the invention are suitability of a gas sensor for detecting different gases including explosive gases, measurement of concentrations in different ranges, reduction of interference signals without diminution of the magnitude of the measurement signal, analysis of residual interference signals for monitoring of sensor operation, and cost-effective and automated manufacture.

In a preferred photo-acoustic gas sensor, components are disposed so that the volume of the measurement chamber can be changed without changing the system size of the sensor and the outer dimensions of the sensor body. Thus, a single type of sensor body with prescribed outer dimensions is sufficient for the realization of different gas sensors with measurement chambers of different sizes. Variable size of the measurement chamber affords measurement of gas concentrations over different measurement ranges and with different sensitivities.

The sensor body consists of a short cylinder. A gas-permeable membrane is disposed on the upper cylinder cover surface of the cylinder, and a circuit board is disposed on the lower cylinder cover surface. The circuit board includes the electrical components required on the sensor proper, namely a light source, a photo-diode and a microphone. These are electrically coupled to a driver and analyzer electronics unit which may be integrated on the same circuit board or mounted on a separate circuit board.

A cylindrical measurement chamber is disposed perpendicular to the cylinder axis of the sensor body, so that the longitudinal axis of the measurement chamber extends parallel to the membrane and the circuit board. The microphone is also disposed laterally to the measurement chamber. The membrane and the circuit board with the light source are disposed opposite one another, with the light source being laterally offset relative to the membrane so that no direct radiation falls onto the membrane.

Preferably, the membrane is disposed on a coarse perforated screen of a few millimeters thickness which imparts sufficient mechanical stability to the membrane so that it cannot be set in oscillation by jarring or by vibrations which would give rise to interference signals. The perforated screen is permeable to gas, but prevents irradiation of the membrane almost completely. Light rays from the light source reach the membrane only after several reflections from the chamber walls, i.e., they are greatly attenuated.

Typically, the light source lies on the longitudinal axis of the measurement chamber, so that the chamber is well illuminated. In the case of a broad-band light source, an optical filter which passes those spectral lines which are absorbed by the gas is disposed between the light source and the measurement chamber.

In this arrangement, the length of the measurement chamber can be extended up to the diameter of the sensor body without a need for changing the height of the sensor body. Thus, the system size can be retained and, advantageously, only one sensor housing is required for sensors with measurement chambers of differing length.

In using a gas sensor in the presence of an explosive gas, e.g., methane, propane, acetone and the like, there is a danger of gas ignition due to short-circuiting of the light source or breakage of the lamp glass. Ignition can be prevented by tightly sealing the light source from the environment. In accordance with an aspect of the invention, the gas sensor is rendered explosion-proof in that the light source and the photo-diode are tightly sealed from the environment by a sealing compound and a sealing cover. The sealing compound seals the light source and photo-diode especially at their plug-in openings. The sealing cover may also serve as a reflector for the light source. For this purpose, its inside is formed as a concave reflector by which the light intensity in the measurement chamber, and thus also the signal magnitude, is increased.

As a result of the offset arrangement of the membrane relative to the light source, irradiation of the membrane is limited to rays which reach the membrane after multiple reflections from the side walls of the measurement chamber. Thus, the membrane causes a minimum of interference signals.

A further interference signal may be produced by the adhesive which bonds the optical filter to the sensor body, i.e., produced even when there is no gas in the measurement chamber. In accordance with an aspect of the invention, this interference signal is analyzed as a monitored background signal for the microphone function. Disappearance of this signal indicates an outage of the microphone.

By the described arrangement, labor required and costs incurred in the manufacture of the gas sensor are reduced. The manufacture of a sensor for a new field of use merely requires a change in the length of the measurement chamber, the other parts of the sensor remaining unchanged. Arrangement of the electrical components on a single circuit board additionally simplifies assembly and adjustment of the components relative to the sensor body. The costs of the components of the sensor are reduced in that the membrane and the optical band-pass filter, both of which are made of costly materials, are cut rectangular or square rather than round. As a result, less material is wasted, and straight-edge cutting is simpler and cheaper.

DETAILED DESCRIPTION OF PREFERRED EMBODIMENTS

Figure 1:
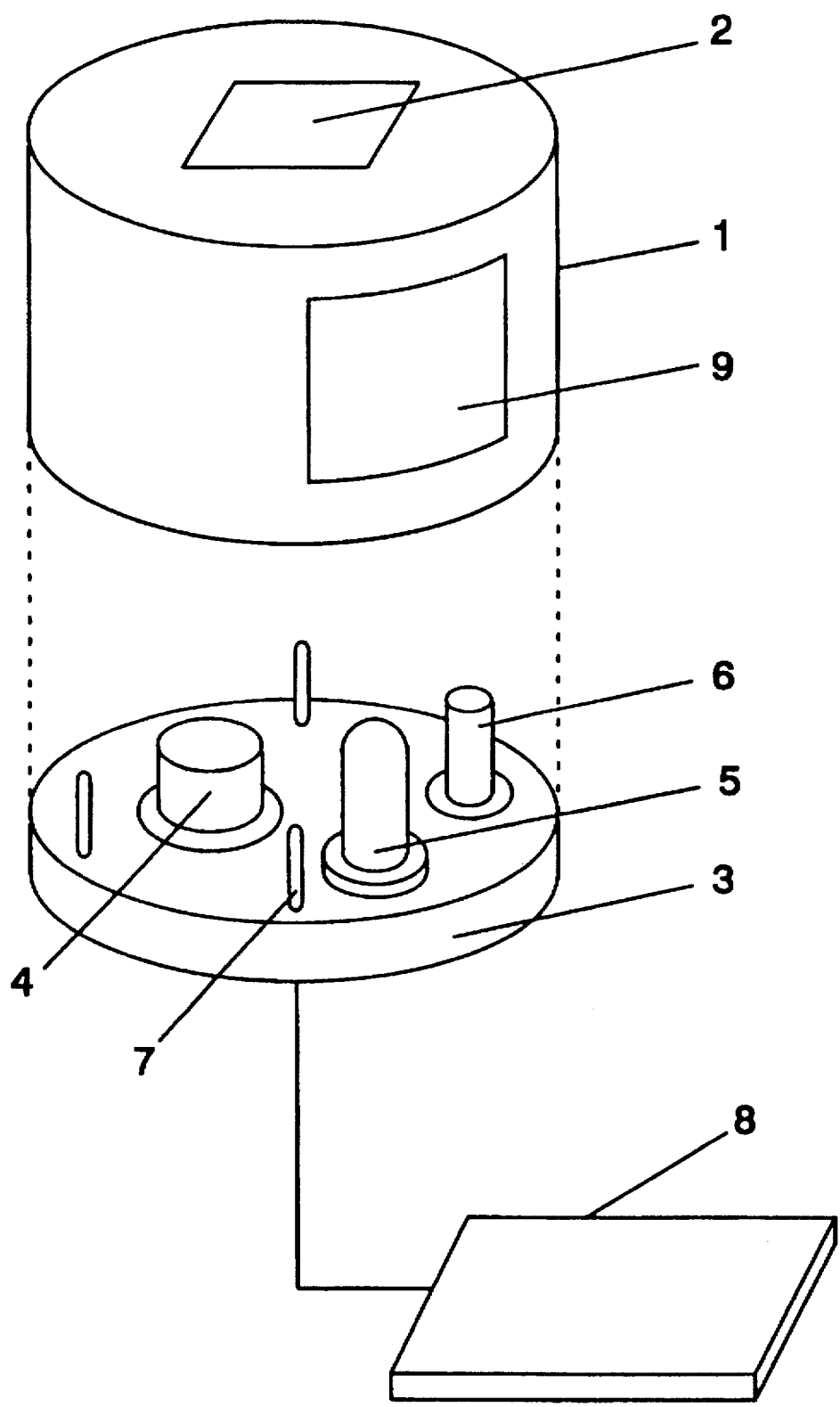
FIG. 1 is a perspective view from above, of a gas sensor with circuit board and electronics unit.

FIG. 1 shows a gas sensor with a cylindrical sensor body 1 which is preferably made of aluminum, for example, or of a similar material which is environmentally stable and non-corroding. A square, gas-permeable membrane 2 is disposed on the upper cylinder cover surface. The membrane 2 consists of a fine-mesh material with openings on the order of nanometers, so that the membrane is permeable to gas but impermeable to water droplets. Disposed on the opposite, lower cylinder cover surface of the cylindrical body 1 is a circuit board 3, here shown downwardly offset to reveal internal components. The circuit board 3 includes a microphone 4, a light source 5 and a photo-diode 6. The light source 5 can be a conventional lamp with a spiral-wound glow filament, or a laser source. The photo-diode 6 consists of a silicon cell and a daylight filter and serves to monitor the intensity of the light emanating from the light-source filament, e.g., in the wavelength range around 900 nm. The filament emits light over a broad spectrum reaching into the infrared range. As a spectral line used for gas detection typically lies in the infrared range, monitoring at a wavelength of 900 nm can be taken as sufficiently reliable for monitoring the light source in the course of gas measurement.

The circuit board 3 has adjustment pins 7 for ready adjustment of the circuit board relative to the sensor body 1 and for attachment by adhesive to the sensor body. The circuit board 3 is connected to a further circuit board which includes a driver and analyzer electronics unit 8. The driver unit causes the lamp to turn on and off in an duty cycle of ⅓, with a switching cycle of approximately 1/10 second.

Heating of the filament, when the lamp is turned on, typically is more rapid than cooling when the lamp is turned off. The operating cycle of ⅓ allows the filament to cool down sufficiently after turn-off. The output signal from the microphone is fed to the analyzer electronics unit 8 by which it is converted to a DC voltage signal by means of a lock-in amplifier and rectifier. Stored calibration values are used to relate signal voltages to gas concentration values.

The sealing cover 9, which renders the sensor explosion-proof, is shown on the cylinder lateral surface of the sensor body 1.

Figure 2:
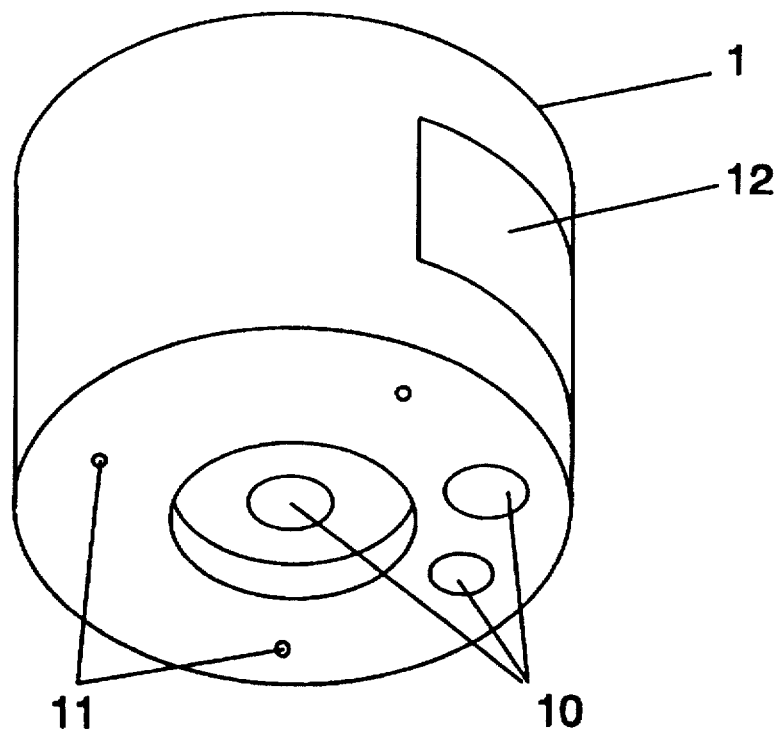
FIG. 2 is a perspective view from below, of the sensor body of the gas sensor. For clarity, the circuit board is not shown.

As shown in FIG. 2, the lower side of the sensor body 1 has three plug-in openings 10 for the microphone 4, the light source 5 and the photo-diode 6. It also has plug-in openings 11 for the adjustment pins 7. The cylinder lateral surface of the sensor body 1 has an opening 12 for the sealing cover 9. Here not visible is the gas-permeable membrane 2 on the upper cylinder cover surface of the sensor body 1.

Figure 3:
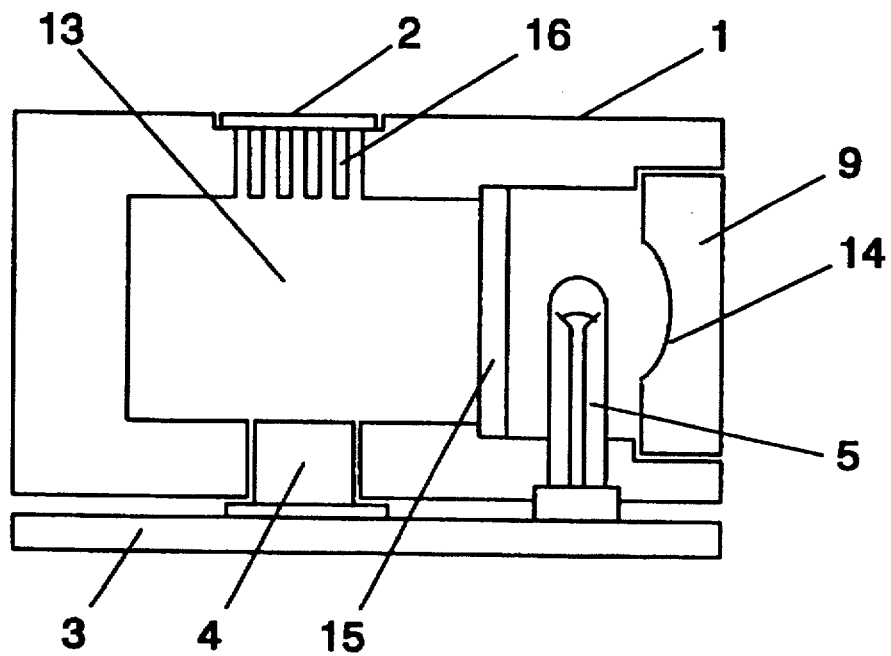
FIG. 3 is a section through the gas sensor along the measurement chamber axis and perpendicular to the membrane surface, showing the light source with the reflector integrated in the sealing cover and its arrangement with respect to the measurement chamber and the gas-permeable membrane.

FIG. 3 shows the light source 5 disposed such that the light-source filament comes to lie on the longitudinal axis of the cylindrical measurement chamber 13. The sealing cover 9, which on its inside has a reflector 14, is disposed behind the light source 5. The reflector 14 is configured such that the light intensity is greatest in the measurement chamber 13. An optical band-pass filter 15 is disposed between the light source 5 and the measurement chamber 13. The filter is adapted to the gas to be detected. E.g., for detection of $CO_2$, the filter is made for transmission of a narrow spectral band around 4.26 μm.

The filter 15 is attached to the sensor body 1 by an adhesive which absorbs visible light. Absorption of this light prevents illumination of the measurement chamber with light of undesired wavelengths. However, the adhesive also produces a background signal as it heats up due to the absorption, producing an acoustic signal. Advantageously, this background signal is used to monitor the functioning of the microphone 4, the light source 5 and the photo-diode 6. Disappearance of this background signal indicates malfunctioning of at least one of these components.

Analysis of a background signal for component monitoring is particularly convenient when a gas is to be detected which is present in the ambient air. For example, in $CO_2$ measurement, the signal of the $CO_2$ present in the air (approx. 0.04%) can be used as background signal. If another gas, e.g., methane is measured which is not present in natural air, the background signal originating from the adhesive can be used for monitoring as described.

Gas enters the measurement chamber through the gas-permeable membrane 2 and a coarse perforated screen 16. The screen 16 also prevents irradiation of the membrane 2 by the light source 5. Few rays can reach the membrane, and, if so, only after several reflections, so that the membrane is negligible as an interference signal source.

If the gas sensor is to be used in another field, for detection of a different gas or of the same gas in a different measurement range, the length of the measurement chamber can be changed in assembly. For each measurement chamber volume, there is a different relationship between the voltage signal and the associated gas concentration. Depending on the size of the measurement chamber, a calibration curve can be defined according to the following equation:

$$y(x; l,r) = A(l,r) + B(l,r) \cdot (1 - e^{-C(l) \cdot x})$$

where y(x; l,r) is the measurement signal in volts, x is the gas concentration in %, l is the length of the measurement chamber, r is the radius of the measurement chamber, A(l,r) is the zero-point signal in volts, B(l,r) is the signal in volts for the maximum concentration minus A(l,r).

C(l) is defined by C(l)=ϵ·l, having dimension (%)$^{-1}$, with ϵ being the percentile natural extinction coefficient in %/mm.

A(l,r) and B(l,r) are constants which depend on the geometry and properties of the measurement chamber. These properties include, e.g., the effects of the side walls on the acoustic signal. The constants are defined as follows:

$$A(l,r) = A(l_0,r_0) \cdot r_0^2 l_0 \cdot (r^2 + 2rl)/r^2 l \cdot (r_0^2 + 2r_0 l_0)$$

$$B(l,r) = B(l_0,r_0) \cdot r_0^2 l_0 / r^2 l$$

The values $l_0$ and $r_0$ are the length and the radius of a chamber with which a measurement of the voltage signals as a function of known gas concentrations is carried out. From known constants A and B for values $l=l_0$ and $r=r_0$, constants for other values of l and r can be calculated, to produce calibration curves of the voltage signal as a function of the gas concentration for different chamber volumes. It has been found that, for long measurement chambers, the curve rises steeply at low gas concentrations, but levels off at higher concentrations where, as a result, measurement resolution is reduced. A shorter measurement chamber with the same radius gives a curve which is steeper still, and which levels off considerably less at higher concentrations. Thus, a shorter measurement chamber affords a higher measurement resolution over a larger measurement range, while a longer measurement chamber is more suitable for the measurement of small gas concentrations. For the measurement of small concentrations, a measurement chamber with a larger volume is advantageous further in that the background signals produced by the side walls are smaller, in accordance with the ratio of chamber volume to side wall surface.

The equation can be used to determine the measurement sensitivity for a given measurement chamber. Conversely, for a desired sensitivity, it can be used to determine a required length of the measurement chamber. In assembly, the constants A, B and C are determined for each gas sensor and stored in an EEPROM (electrically erasable programmable read-only memory), for example. With the aid of these stored values, gas concentrations can be determined from the voltage signals.

If the measurement chamber is to be reduced to a very short length, it is necessary further to take into account the ratio of membrane surface to chamber volume in the equation. In this case, if this ratio becomes very large, the size of the voltage signals is reduced.

An example of the measurement sensitivity as a function of the measurement chamber volume is as follows: A gas sensor as described, with a measurement chamber length of 11 mm and a chamber radius of 5 mm indicates a $CO_2$-concentration of 1% by a voltage signal of 3 V. With this chamber size, the resolution at higher concentrations is poor. A sensor with the same chamber radius and a reduced chamber length of 3 mm indicates the 1%-concentration by a voltage signal of 6 V, but affords measurement of gas concentrations greater than 5% with good resolution.

An example of feasible measurement ranges of a gas sensor for the detection of $CO_2$ with a predetermined sensor body size is as follows: A sensor body has a diameter of 25 mm and includes a measurement chamber with a constant radius of 5 mm. Measurement chamber length can range from 3 mm to 20 mm, for example. From the equation it can be determined that the smallest measurement range is for gas concentrations from 0% to 0.2% and the largest for gas concentrations from 0% to 10%.

We claim:

1. A photo-acoustic gas sensor for measuring a gas concentration, comprising:
    a cylindrical sensor body having a longitudinal axis, an upper cover, a lower cover and a cylinder lateral surface;
    a cylindrical measurement chamber disposed within the sensor body;
    a gas-permeable membrane attached to the upper cover of the sensor body, for admitting a gas to the measurement chamber;
    a light source for illuminating the measurement chamber with intensity-modulated light, a microphone for detecting pressure waves in the measurement chamber, and a photo-diode for monitoring the light source attached to the lower cover of the cylindrical sensor body; and
    coupling means for electrically coupling the light source, the photo-diode and the microphone to a control and analyzer electronics unit;
    wherein the measurement chamber has a longitudinal axis which is perpendicular to the longitudinal axis of the cylindrical sensor body, and the light source is disposed for illuminating the measurement chamber in its longitudinal direction and is offset laterally relative to the gas-permeable membrane, for the gas-permeable membrane to remain substantially free of radiation.

2. The photo-acoustic gas sensor of claim 1, wherein the light source is a broad-band light source, with the photo-acoustic sensor further comprising an optical band-pass filter between the light source and the measurement chamber, with spectral transmission of the filter corresponding to an absorption line of a gas to be detected.

3. The photo-acoustic gas sensor according to claim 2, wherein the optical band-pass filter is attached to the sensor body by a light-absorbent adhesive which prevents leakage into the measurement chamber of unfiltered light along the edges of the band-pass filter.

4. The photo-acoustic gas sensor according to claim 2, wherein the optical band-pass filter is rectangular.

5. The photo-acoustic gas sensor according to claim 1, further comprising a sealing cover on the cylinder lateral surface and a sealing compound, thereby protecting the light source and the photo-diode from the ambient and rendering the gas sensor explosion-proof.

6. The photo-acoustic gas sensor according to claim 5, wherein the sealing cover is configured on its inside as a reflector for reflecting light from the light source into the measurement chamber.

7. The photo-acoustic gas sensor according to claim 1, wherein the gas-permeable membrane is rectangular.

8. The photo-acoustic gas sensor according to claim 1, wherein the light source, the photo-diode and the microphone are mounted on a common circuit board comprising pins for adjusting and attaching the circuit board to the sensor body.

9. A method for photo-acoustic gas sensing, comprising:
    illuminating a measurement volume with modulated optical radiation having a predetermined wavelength;
    detecting an acoustic pressure wave generated by the optical radiation; and
    analyzing the acoustic pressure wave for a background signal originating with a light-absorbent adhesive, for monitoring functioning of an illuminating light source, a detector microphone, and a light-source-monitor photo-diode.

10. The photo-acoustic gas sensor of claim 1, wherein the upper cover of the sensor body comprises a perforated screen, and wherein attachment of the gas-permeable membrane is to the perforated screen.

11. The photo-acoustic gas sensor according to claim 1, wherein the cylindrical measurement chamber is dimensioned for a desired measurement sensitivity, and wherein the cylindrical sensor body has a diameter such that the length of the cylindrical measurement chamber is less than the diameter of the cylindrical sensor body.

12. The photo-acoustic gas sensor according to claim 1 in combination with a control and analyzer electronics unit to which the coupling means of the gas sensor is electrically coupled, wherein the control and analyzer electronics unit comprises an EEPROM for storing gas sensor calibration data which relate gas sensor signal voltage values to gas concentration values.

* * * * *

UNITED STATES PATENT AND TRADEMARK OFFICE
CERTIFICATE OF CORRECTION

PATENT NO. : 5,753,797
DATED : May 19, 1998
INVENTOR(S) : Forster et al.

It is certified that error appears in the above-identified patent and that said Letters Patent is hereby corrected as shown below:

On the title page, under "U.S. PATENT DOCUMENTS", the following patent should have been inserted:

--4,372,149  2/1983  Zharov...........73/24.02--.

Signed and Sealed this

Ninth Day of May, 2000

Attest:

Q. TODD DICKINSON

Attesting Officer                Director of Patents and Trademarks